(12) United States Patent
Hart et al.

(10) Patent No.: US 10,966,779 B2
(45) Date of Patent: Apr. 6, 2021

(54) BIPOLAR SURGICAL INSTRUMENT

(71) Applicant: COVIDIEN LP, Mansfield, MA (US)

(72) Inventors: Keir Hart, Lafayette, CO (US);
Rebecca J. Coulson, Lyons, CO (US);
Gary M. Couture, Ward, CO (US);
Geneva Ladtkow, Arvada, CO (US);
Weng-Kai K. Lee, Longmont, CO (US); Kenneth E. Netzel, Loveland, CO (US); Prakash Manley, Lafayette, CO (US); Arlen J. Reschke, Longmont, CO (US); Anthony D. Ricke, Boulder, CO (US); Jeffrey R. Townsend, Longmont, CO (US)

(73) Assignee: Covidien LP, Mansfield, MA (US)

(*) Notice: Subject to any disclaimer, the term of this patent is extended or adjusted under 35 U.S.C. 154(b) by 556 days.

(21) Appl. No.: 14/904,649

(22) PCT Filed: Aug. 7, 2013

(86) PCT No.: PCT/CN2013/080944
§ 371 (c)(1),
(2) Date: Jan. 12, 2016

(87) PCT Pub. No.: WO2015/017989
PCT Pub. Date: Feb. 12, 2015

(65) Prior Publication Data
US 2016/0143687 A1    May 26, 2016

(51) Int. Cl.
*A61B 18/14* (2006.01)
*A61B 18/00* (2006.01)
(Continued)

(52) U.S. Cl.
CPC ...... *A61B 18/1442* (2013.01); *A61B 18/1206* (2013.01); *A61B 2017/00526* (2013.01);
(Continued)

(58) Field of Classification Search
CPC ...... A61B 18/1442; A61B 2017/00438; A61B 2017/2939; A61B 2018/00589;
(Continued)

(56) References Cited

U.S. PATENT DOCUMENTS

D249,549 S    9/1978  Pike
D263,020 S    2/1982  Rau, III
(Continued)

FOREIGN PATENT DOCUMENTS

CN    201299462         9/2009
DE      2415263 A1     10/1975
(Continued)

OTHER PUBLICATIONS

U.S. Appl. No. 08/926,869, filed Sep. 10, 1997, James G. Chandler.
(Continued)

*Primary Examiner* — Michael F Peffley
*Assistant Examiner* — Tigist S Demie
(74) *Attorney, Agent, or Firm* — Carter, DeLuca & Farrell LLP

(57) ABSTRACT

A bipolar forceps includes a mechanical forceps including first and second shafts each having a jaw member extending from a distal end thereof and a handle disposed at a proximal end thereof for effecting movement of the jaw members relative to one another about a pivot. A disposable housing is configured to releasably couple to at least one of the shafts and an electrode assembly has electrodes releasably coupleable to the jaw members and adapted to connect to a source of electrosurgical energy to allow selective conduction of electrosurgical energy through tissue held therebetween to effect a tissue seal. An electrically conductive cutting element is disposed on at least one of the electrodes and is adapted to connect to the source of electrosurgical energy to
(Continued)

allow selective conduction of electrosurgical energy through tissue held between the electrodes to effect a tissue cut.

20 Claims, 7 Drawing Sheets

(51) Int. Cl.
*A61B 18/12* (2006.01)
*A61B 17/00* (2006.01)

(52) U.S. Cl.
CPC ............ *A61B 2018/0063* (2013.01); *A61B 2018/00083* (2013.01); *A61B 2018/00345* (2013.01); *A61B 2018/00601* (2013.01); *A61B 2018/00607* (2013.01); *A61B 2018/126* (2013.01); *A61B 2018/1452* (2013.01); *A61B 2018/1457* (2013.01); *A61B 2018/1495* (2013.01)

(58) Field of Classification Search
CPC ........... A61B 2018/00607; A61B 2018/00619; A61B 2018/0063; A61B 2018/00922; A61B 2018/128; A61B 2018/1455
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| 5,304,203 A | 4/1994 | El-Mallawany et al. |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,578,052 A | 11/1996 | Koros et al. |
| 5,618,294 A | 4/1997 | Aust et al. |
| D384,413 S | 9/1997 | Zlock et al. |
| 5,665,100 A | 9/1997 | Yoon |
| H1745 H | 8/1998 | Paraschac |
| 5,814,043 A | 9/1998 | Shapeton |
| D402,028 S | 12/1998 | Grimm et al. |
| D408,018 S | 4/1999 | McNaughton |
| D416,089 S | 11/1999 | Barton et al. |
| 6,050,996 A | 4/2000 | Schmaltz et al. |
| D424,694 S | 5/2000 | Tetzlaff et al. |
| D425,201 S | 5/2000 | Tetzlaff et al. |
| 6,068,628 A * | 5/2000 | Fanton ............ A61B 17/32001 606/28 |
| H1904 H | 10/2000 | Yates et al. |
| 6,293,954 B1 | 9/2001 | Fogarty et al. |
| D449,886 S | 10/2001 | Tetzlaff et al. |
| 6,329,778 B1 | 12/2001 | Culp et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,406,485 B1 | 6/2002 | Hossain et al. |
| H2037 H | 7/2002 | Yates et al. |
| 6,464,704 B2 | 10/2002 | Schmaltz et al. |
| D465,281 S | 11/2002 | Lang |
| D466,209 S | 11/2002 | Bon |
| 6,511,480 B1 | 1/2003 | Tetzlaff et al. |
| 6,673,092 B1 | 1/2004 | Bacher |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| 7,118,570 B2 | 10/2006 | Tetzlaff et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,329,257 B2 | 2/2008 | Kanehira et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swayer et al. |
| 7,641,653 B2 | 1/2010 | Dalla Betta et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 9,028,492 B2 | 5/2015 | Kerr et al. |
| 2003/0018332 A1 | 1/2003 | Schmaltz et al. |
| 2003/0109875 A1 | 6/2003 | Tetzlaff et al. |
| 2003/0229344 A1 | 12/2003 | Dycus et al. |
| 2005/0113826 A1* | 5/2005 | Johnson ............ A61B 18/1442 606/45 |
| 2005/0113828 A1 | 5/2005 | Shields et al. |
| 2006/0253126 A1 | 11/2006 | Bjerken et al. |
| 2006/0271038 A1 | 11/2006 | Johnson et al. |
| 2007/0062017 A1 | 3/2007 | Dycus et al. |
| 2007/0260241 A1 | 11/2007 | Dalla Betta et al. |
| 2008/0058802 A1* | 3/2008 | Couture ............ A61B 18/1442 606/48 |
| 2009/0131934 A1 | 5/2009 | Odom et al. |
| 2010/0016857 A1 | 1/2010 | McKenna et al. |
| 2010/0228250 A1 | 9/2010 | Brogna |
| 2010/0292691 A1 | 11/2010 | Brogna |
| 2010/0305567 A1 | 12/2010 | Swanson |
| 2011/0072638 A1 | 3/2011 | Brandt et al. |
| 2012/0083785 A1 | 4/2012 | Roy et al. |
| 2013/0018411 A1* | 1/2013 | Collings ............ A61B 17/285 606/205 |
| 2013/0041370 A1 | 2/2013 | Unger |
| 2016/0157925 A1 | 6/2016 | Artale et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| EP | 2353535 A1 | 8/2011 |
| EP | 2428177 A1 | 3/2012 |
| JP | 61-501068 | 9/1984 |
| JP | 10-24051 A | 1/1989 |

(56) References Cited

FOREIGN PATENT DOCUMENTS

| JP | 11-47150 A | 6/1989 |
|---|---|---|
| JP | 6502328 | 3/1992 |
| JP | 5-5106 | 1/1993 |
| JP | 05-40112 | 2/1993 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 3/1996 |
| JP | 08252263 A | 10/1996 |
| JP | 8-317934 A | 12/1996 |
| JP | 9-10223 | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001029356 A | 2/2001 |
| JP | 2001128990 A | 5/2001 |
| JP | 2001-190564 A | 7/2001 |
| JP | 2004-517668 A | 6/2004 |
| JP | 2004-528869 A | 9/2004 |
| SU | 401367 A1 | 10/1973 |
| WO | 94/00059 | 1/1994 |
| WO | 99-23933 A2 | 5/1999 |
| WO | 00/24330 | 5/2000 |
| WO | 0036986 A1 | 6/2000 |
| WO | 0115614 A1 | 3/2001 |
| WO | 0154604 A1 | 8/2001 |
| WO | 02/080793 | 10/2002 |
| WO | 02080786 A1 | 10/2002 |
| WO | 2005/110264 A2 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Homer.
U.S. Appl. No. 12/769,444, filed Apr. 28, 2010, Glenn A. Homer.
U.S. Appl. No. 12/770,369, filed Apr. 29, 2010, Glenn A. Homer.
U.S. Appl. No. 12/770,380, filed Apr. 29, 2010, Glenn A. Homer.
U.S. Appl. No. 12/770,387, filed Apr. 29, 2010, Glenn A. Homer.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Homer.
U.S. Appl. No. 12/792,051, filed Jun. 2, 2010, David M. Garrison.
U.S. Appl. No. 12/792,068, filed Jun. 2, 2010, Glenn A. Homer.
U.S. Appl. No. 12/792,097, filed Jun. 2, 2010, Duane E. Kerr.
U.S. Appl. No. 12/792,262, filed Jun. 2, 2010, Jeffrey M. Roy.

U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
Extended European Search Report issued in Appl. No. EP 13891082.3 dated Mar. 24, 2017.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" Innovations That Work, .quadrature.June 2003.
Chung et al., "Clinical Experience of Sutureless Closed Hemorrhoidectomy with LigaSure" Diseases of the Colon & Rectum vol. 46, No. 1 Jan. 2003.

(56) References Cited

OTHER PUBLICATIONS

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicoletomy Using the LigaSure Vessel Sealing System" Innovations That Work,. quadrature.Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,.quadrature. Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson. "Use of the LigaSure Vessel Sealing System in Bloodless Hemorrhoidectomy" That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrell et al., "Use of the LigaSure Vessel Sealing System for Perl-Hilar Vessels in Laparoscopic Nephrectomy" Sales Product Literature.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
International Search Report and Written Opinion of the International Searching Authority dated Jan. 17, 2013 from counterpart International Application No. PCT/US2012/050094 (8 pgs.).
European Search Report, dated Feb. 19, 2015, corresponding to European Patent Application No. 12824142.9; 6 pages.
European Extended Search Report dated Jun. 29, 2015, corresponding to European Application No. 12824142.9; 10 pages.
English translation of first Chinese Office Action and Search Report dated Aug. 28, 2015, corresponding to Chinese Patent Application No. 201280035427.4; 9 total pages.

\* cited by examiner

BIPOLAR SURGICAL INSTRUMENT

CROSS REFERENCE TO RELATED APPLICATION

The present application is a U.S. National Stage Application under 35 U.S.C. § 371(a) of PCT/CN2013/080944 filed Aug. 7, 2013, the entire contents of which are incorporated by reference herein.

BACKGROUND

1. Background of Related Art

The present disclosure relates to forceps used for open surgical procedures. More particularly, the present disclosure relates to a bipolar forceps for treating tissue that is capable of sealing and cutting tissue.

2. Technical Field

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Certain surgical procedures require sealing and cutting blood vessels or vascular tissue. Several journal articles have disclosed methods for sealing small blood vessels using electrosurgery. An article entitled Studies on Coagulation and the Development of an Automatic Computerized Bipolar Coagulator, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled Automatically Controlled Bipolar Electrocoagulation—"COA-COMP", Neurosurg. Rev. (1984), pp. 187-190, describes a method for terminating electrosurgical power to the vessel so that charring of the vessel walls can be avoided.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

SUMMARY

The present disclosure relates to forceps used for open surgical procedures. More particularly, the present disclosure relates to a bipolar forceps for electrosurgically sealing and cutting tissue.

As is traditional, the term "distal" refers herein to an end of the apparatus that is farther from an operator, and the term "proximal" refers herein to the end of the electrosurgical forceps that is closer to the operator.

According to one aspect of the present disclosure, a bipolar forceps is provided. The bipolar forceps generally includes a mechanical forceps, a disposable housing, an electrode assembly, and an electrically conductive cutting element. The mechanical forceps includes first and second shafts each having a jaw member extending from its distal end and a handle disposed at its proximal end for effecting movement of the jaw members relative to one another about a pivot from a first position wherein the jaw members are disposed in spaced relation relative to one another to a second position wherein the jaw members cooperate to grasp tissue. The disposable housing is configured to releasably couple to at least one of the shafts. The electrode assembly has a first electrode releasably coupleable to the jaw member of the first shaft and a second electrode releasably coupleable to the jaw member of the second shaft. Each electrode is adapted to connect to a source of electrosurgical energy to allow selective conduction of electrosurgical energy through tissue to effect a tissue seal. The electrically conductive cutting element is disposed on one or both of the electrodes and is adapted to connect to the source of electrosurgical energy to allow selective conduction of electrosurgical energy through tissue held between the electrodes to effect a tissue cut.

Additionally or alternatively, one or both of the electrodes may include a channel defined along its length in vertical registration with the conductive cutting element and configured to engage the conductive cutting element when the jaw members are in the second position to provide a gap distance between the electrodes.

Additionally or alternatively, the conductive cutting element may extend from the electrode thereof a distance between about 0.004" and about 0.010" and the channel may define a depth of up to about 0.006".

Additionally or alternatively, the extension distance of the conductive cutting element and the depth of the channel may cooperate to provide a gap distance of about 0.004".

Additionally or alternatively, the bipolar forceps may also include one or more switches disposed through the housing and configured to selectively deliver electrosurgical energy to one or both of the electrically conductive cutting element and the electrodes.

Additionally or alternatively, the switch may be configured to selectively deliver electrosurgical energy to the electrodes and the electrically conductive cutting element in response to a single activation of the switch.

Additionally or alternatively, each of the electrodes may include an electrically conductive sealing surface and at least one insulating substrate.

Additionally or alternatively, a ratio of a prominence of the conductive cutting element to half a width of the electrically conductive sealing surface of the electrode thereof is between about 0.25 and about 0.30.

Additionally or alternatively, the conductive cutting element may define a base portion and a body portion. The base portion may define a width of at least 0.022" and the body may define a minimum width of about 0.015".

Additionally or alternatively, the pivot may include a first surface configured to be received in an aperture defined through the first jaw member and a second surface configured to be received in an aperture defined through the second jaw member.

Additionally or alternatively, each of the electrodes may include one or more mechanical interfaces configured to complement a corresponding mechanical interface on one of the jaw members to releasably couple the electrode to the respective jaw member.

Additionally or alternatively, the bipolar forceps may also include a tissue stop disposed at a proximal end of one or both of the jaw members and configured to maintain tissue between the electrodes during tissue sealing.

According to another aspect of the present disclosure, a bipolar forceps is provided. The bipolar forceps generally includes a mechanical forceps, a disposable housing, an electrode assembly, an electrically conductive cutting element, one or more channels, and one or more switches. The mechanical forceps including first and second shafts each having a jaw member extending from its distal end and a handle disposed at its proximal end for effecting movement of the jaw members relative to one another about a pivot from a first position wherein the jaw members are disposed in spaced relation relative to one another to a second position wherein the jaw members cooperate to grasp tissue. The disposable housing has opposing halves configured to be releasably coupled to each other to at least partially encompass one or both of the shafts. The electrode assembly has a first electrode releasably coupleable to the jaw member of the first shaft and a second electrode releasably coupleable to the jaw member of the second shaft. Each electrode is adapted to connect to a source of electrosurgical energy to allow selective conduction of electrosurgical energy through tissue to effect a tissue seal. The electrically conductive cutting element is disposed on one or both of the electrodes and is adapted to connect to the source of electrosurgical energy to allow selective conduction of electrosurgical energy through tissue held between the electrodes to effect a tissue cut. The channel is defined along a length of one or both of electrodes and is in vertical registration with the conductive cutting element. The conductive cutting element is configured to engage the channel when the jaw members are in the second position to provide a gap distance between the electrodes. The switch is disposed on the housing and is configured to selectively deliver electrosurgical energy to one or both of the electrically conductive cutting element and the electrodes.

Additionally or alternatively, the switch may be configured to selectively deliver electrosurgical energy to the electrodes and the electrically conductive cutting element in response to a single activation thereof.

Additionally or alternatively, the source of electrosurgical energy may be configured to emit a first audible tone in response to completion of the tissue seal and a second audible tone in response to completion of cutting of the sealed tissue.

Additionally or alternatively, at least a portion of the jaw members are separated by the pivot.

According to another aspect of the present disclosure, a method of manufacturing forceps is provided. The method includes press-fitting a first surface of a pivot into an aperture defined in a first shaft member and pressing a second surface of the pivot into an aperture defined through a first jaw member disposed on a second shaft member. The method also includes pressing a third surface of the pivot into an aperture defined through a second jaw member such that at least a portion of the pivot is disposed between at least a portion of the first and second jaw members to provide separation therebetween. The method also includes coupling a distal end portion of the first shaft member to the second jaw member.

Additionally or alternatively, the method may include coupling an electrode to one or both of the jaw members. The electrode may include one or more of a tissue sealing surface, an insulative substrate, and an electrically conductive cutting element.

Additionally or alternatively, the method may also include welding the distal end portion of the first shaft member to the second jaw member.

Additionally or alternatively, the method may also include coupling a housing to one or both of the shaft members.

BRIEF DESCRIPTION OF THE DRAWINGS

Various embodiments of the subject instrument are described herein with reference to the drawings wherein.

DETAILED DESCRIPTION

Figure 1:
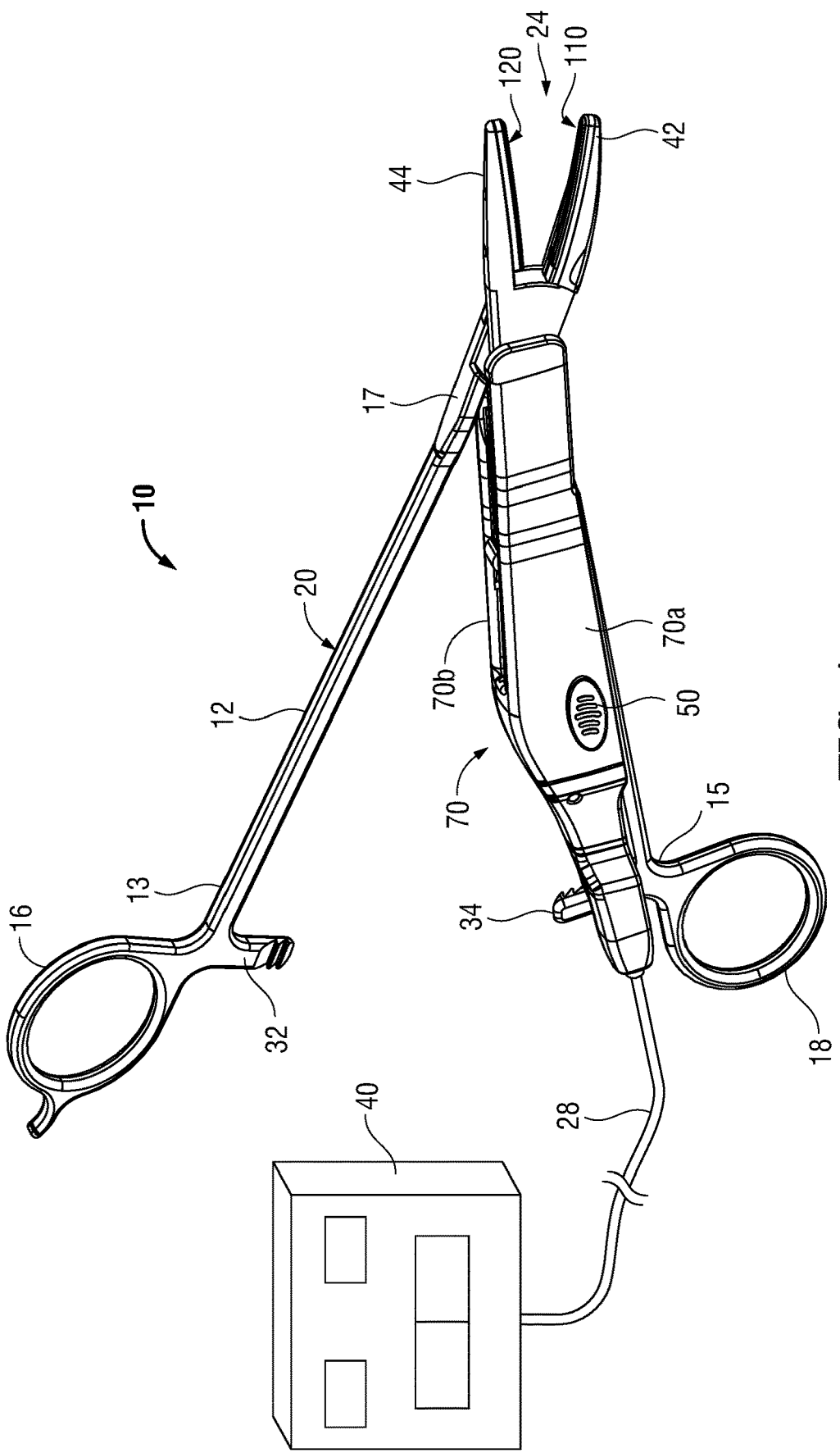
FIG. 1 is a perspective view of a bipolar forceps according to an embodiment of the present disclosure including a mechanical forceps, a disposable housing, and an electrode assembly.
Figure 2:
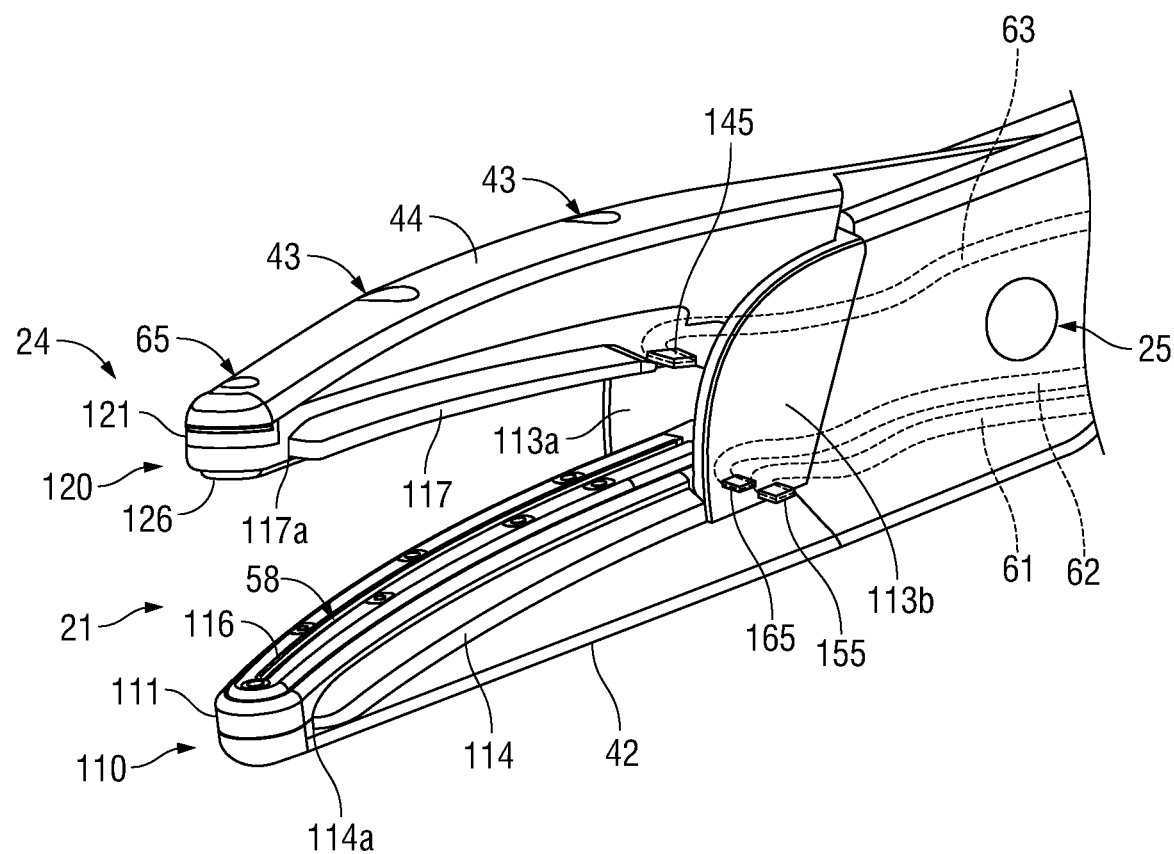
FIG. 2 is an enlarged, perspective view of a distal end of the bipolar forceps of FIG. 1.
Figure 3:
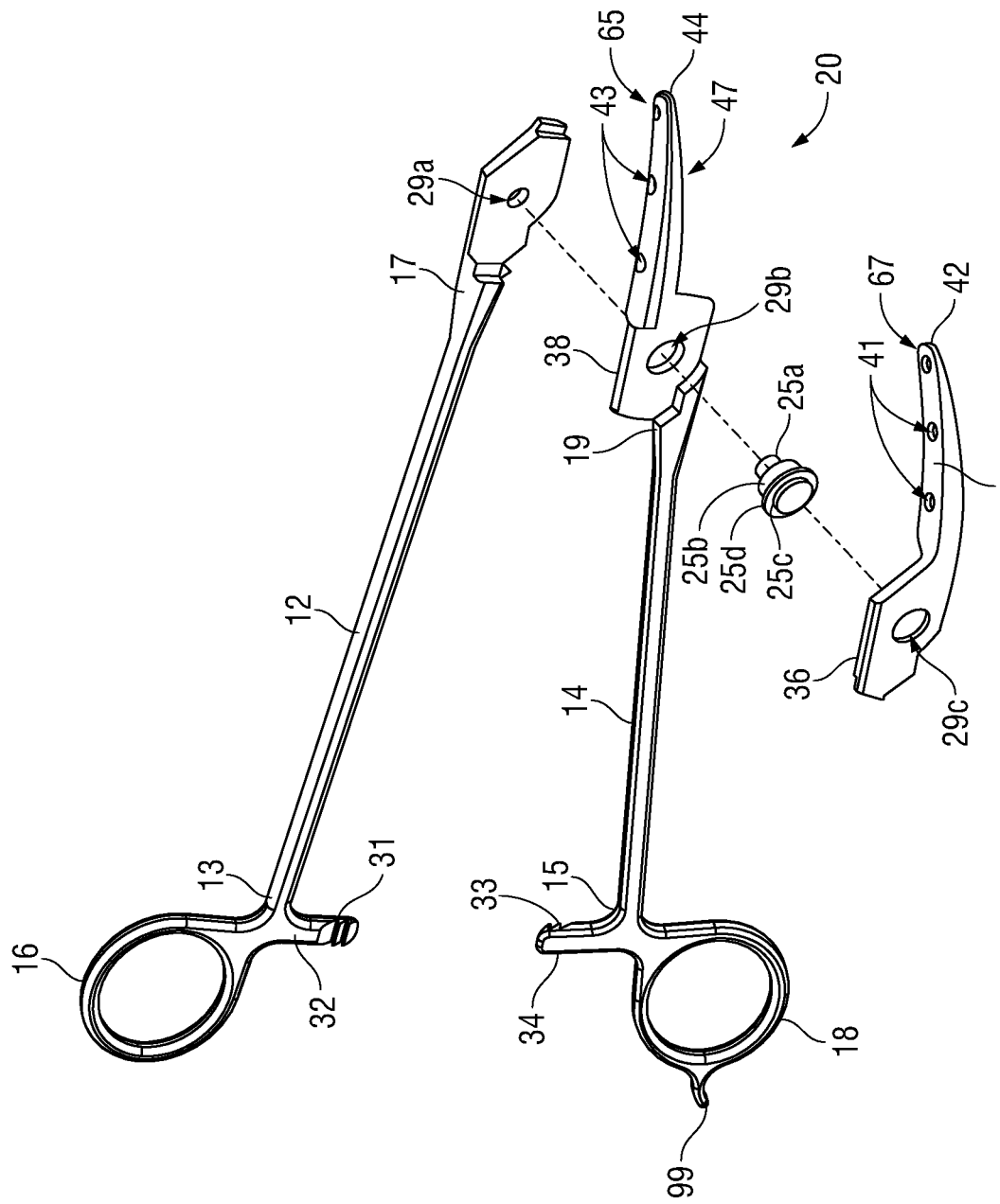
FIG. 3 is a perspective view of the mechanical forceps of FIG. 1 with parts separated.

Referring initially to FIGS. 1-3, a bipolar forceps 10 for use with open and/or laparoscopic surgical procedures includes a mechanical forceps 20 having an end effector 24 and a disposable electrode assembly 21 (FIG. 2). Mechanical forceps 20 includes first and second elongated shaft members 12 and 14. Elongated shaft member 12 includes proximal and distal end portions 13 and 17, respectively, and elongated shaft member 14 includes proximal and distal end portions 15 and 19, respectively. Disposed at proximal end portions 13, 15 of shaft members 12, 14 are handle members 16 and 18, respectively, that are configured to allow a user to effect movement of at least one of the shaft members 12 and 14 relative to the other. The end effector 24 includes opposing jaw members 42, 44 that extend from the distal end portions 17 and 19 of shaft members 12 and 14, respectively. The jaw members 42, 44 are movable relative to each other in response to movement of shaft members 12, 14.

Figure 6:
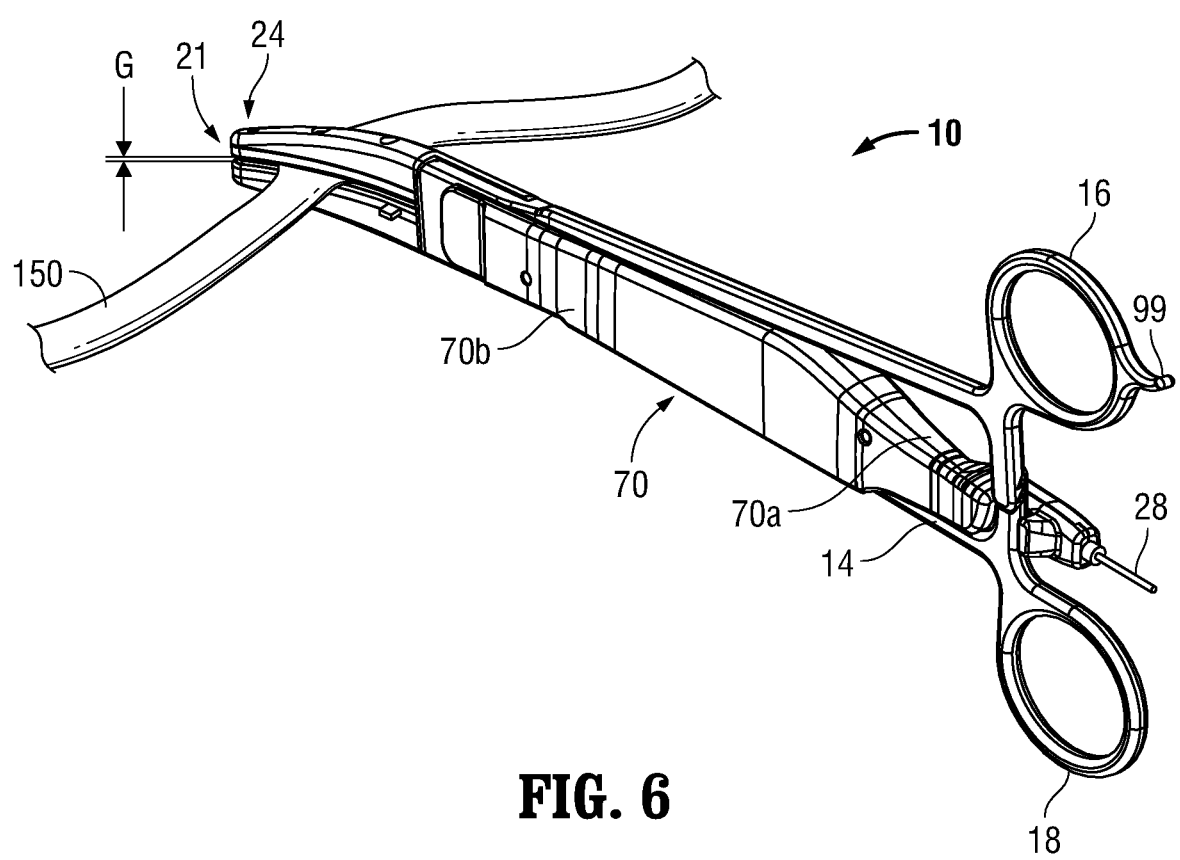
FIG. 6 is a perspective view of the bipolar forceps of FIG. 1 grasping tissue to effect a tissue seal.

Shaft members 12 and 14 are affixed to one another about a pivot 25 such that movement of shaft members 12, 14, imparts movement of the jaw members 42, 44 from an open configuration (FIG. 2) wherein the jaw members 44, 42 are disposed in spaced relation relative to one another to a clamping or closed configuration wherein the jaw members 42, 44 cooperate to grasp tissue 150 therebetween (FIG. 6). In some embodiments, forceps 10 may be configured such that movement of one or both of shaft members 12, 14 causes only one of the jaw members to move with respect to the other jaw member. As further detailed below, pivot 25 serves to sufficiently space the distal end portions 17, 19 of shaft members 12, 14, respectively, from each other to provide clearance therebetween during movement of shaft members 12, 14 about pivot 25.

Each shaft member 12 and 14 also includes a ratchet portion 32 and 34, respectively. Each ratchet 32, 34 extends from the proximal end portion 13, 15 of its respective shaft member 12, 14 towards the other ratchet in a generally vertically aligned manner such that the inner facing surfaces of each ratchet 32 and 34 abut one another when the shaft members 12, 14 are approximated. Each ratchet 32 and 34 includes a plurality of flanges 31 and 33 (FIG. 3), respectively, that project from the inner facing surface of each ratchet 32 and 34 such that the ratchets 32 and 34 may interlock at one or more positions. In some embodiments, each ratchet position holds a particular strain energy in the shaft members 12 and 14 to impart a specific closure force to the end effector 24. At least one of the shaft members, e.g., shaft member 12, includes a tang 99 that facilitates manipulation of forceps 20 during surgical conditions.

A housing 70 having a pair of housing halves 70a, 70b is configured to matingly engage and releasably encompass at least a portion of shaft member 14. An interior of each of housing half 70a, 70b may include a plurality of cooperating mechanical interfaces disposed at various positions to effect mechanical coupling of housing halves 70a, 70b to form housing 70.

Forceps 10 includes an electrical cable 28 extending from housing 70 configured to electrically connect forceps 10 to a source of electrosurgical energy, such as an electrosurgical generator 40, as shown in FIG. 1. One example of an electrosurgical generator is the LIGASURE® Vessel Sealing Generator and the ForceTriad® Generator sold by Covidien.

With reference to FIG. 3, jaw members 42 and 44 include flanges 36 and 38, respectively, extending proximally from a distal portion thereof. Each of flanges 36 and 38 defines a bearing aperture 29c and 29b, respectively, defined therethrough. Pivot 25 includes a press-fit surface 25a and a pair of bearing surfaces 25b and 25c that extend from opposing sides of a clearance surface 25d. Press-fit surface 25a is configured to be press-fit into an aperture 29a defined through a distal end portion 17 of shaft member 12. Bearing surfaces 25b and 25c are configured to be pressed into bearing apertures 29b and 29c, respectively, defined through flanges 38 and 36, respectively. Once shaft members 12, 14 are coupled together about pivot 25, pivot may be secured to shaft members 12, 14 via a suitable welding technique. Shaft members 12, 14 are configured to rotate about pivot 25 such that bearing apertures 29b, 29c pivot about respective bearing surfaces 25b, 25c.

Figure 5:
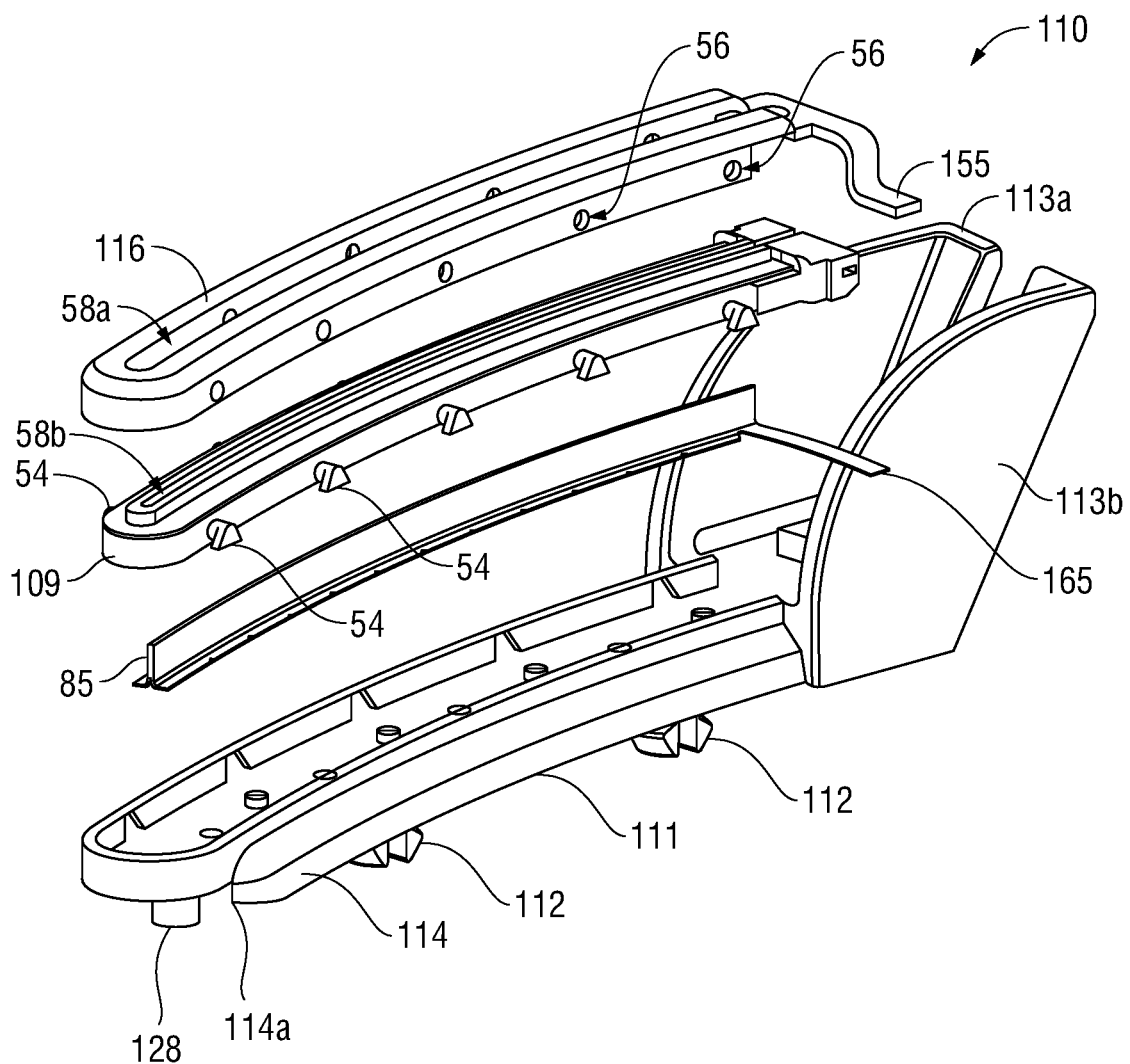

In some embodiments, mechanical forceps 20 may be assembled as follows: Press-fit surface 25a is inserted through aperture 29b such that press-fit surface 25a is press-fit into aperture 29a defined through distal end portion 17 of shaft member 12 and bearing surface 25b is pressed into bearing aperture 29b defined through flange 38 such that clearance surface 25d engages a surface of distal end portion 17 that surrounds bearing aperture 29b. Bearing surface 25c is pressed into bearing aperture 29c defined through flange 36 of jaw member 42 such that clearance surface 25d engages a surface of flange 36 that surrounds bearing aperture 29c and is disposed between flanges 36 and 38. The term "pressed" may refer to any suitable coupling of bearing surfaces 25b, 25c to bearing apertures 29b, 29c, respectively, such as an interface-fit (press-fit, friction-fit, etc.), a transition fit, or a sliding fit. Clearance surface 25d serves to maintain clearance between flanges 36, 38 during pivoting of jaw members 42, 44 about pivot between the open and closed configurations. Clearance surface 25d also serves to limit the distance by which the flanges 36, 38 may be compressed together during assembly of mechanical forceps 20. Once pivot 25 is properly fitted within apertures 29a, 29b, and 29c, as described hereinabove, jaw member 42 may be coupled to distal end portion 17 of shaft member 12. For example, jaw member 42 may be welded along one or more lap joints to distal end portion 17 of shaft member 12. In some embodiments, jaw member 42 may be monolithically formed with shaft member 12 as similarly depicted with respect to jaw member 44 and shaft member 14 (FIG. 3). The term "pressing" refers herein to any suitable interface-fit between Referring to FIG. 2, disposable electrode assembly 21 includes a pair of electrodes 110, 120 configured to releasably couple to mechanical forceps 20, as detailed below. With reference to FIG. 5, electrode 110 includes an electrically conductive sealing surface 116 configured to conduct electrosurgical energy through tissue to effect a tissue seal, an electrically conductive cutting element 85 configured to cut tissue by conducting electrosurgical energy therethrough, and a pair of electrically insulative substrates 109 and 111. In some embodiments, substrates 109, 111 may be made from an injection molded plastic material. Substrate 109 is disposed between sealing surface 116 and cutting element 85 and serves to electrically insulate sealing surface 116 from cutting element 85. Substrate 111 serves to electrically insulate jaw member 44 from sealing surface 116 and cutting element 85. A cutting element channel 58a is defined in sealing surface 116 and is configured to align in vertical registration with a corresponding cutting element channel 58b defined in substrate 109. Cutting element 85 is disposed between substrate 109 and substrate 111 and extends through cutting element channels 58a and 58b such that cutting element 85 extends beyond or is raised above a tissue contacting portion of sealing surface 116. Substrate 109 includes retention features 54 formed thereon configured to be received within corresponding retaining apertures 56 disposed along an outer periphery of sealing surface 116 (FIG. 5) to couple sealing surface 116 to substrate 109. During assembly of electrode 110, sealing surface 116 is coupled to substrate 109 and cutting element 85 is disposed between substrate 109 and substrate 111 such that cutting element 85 extends through channels 58a, 58b. Substrate 111 is subsequently overmolded to the retention features 54 formed on substrate 109 to secure sealing surface 116 to substrate 111.

Substrate 111 includes a plurality of bifurcated anchor members 112 extending therefrom that are configured to compress during insertion into a corresponding plurality of sockets 43 disposed at least partially through an inner facing surface 47 (FIG. 3) of jaw member 44 and subsequently expand to releasably engage corresponding sockets 43 after insertion to couple electrode 110 to inner facing surface 47. Substrate 111 also includes an alignment pin 128 (FIG. 4) that is configured to engage an aperture 65 disposed at least partially through inner facing surface 47 of jaw member 44 to ensure proper alignment of electrode 110 with jaw member 44 during assembly. Sealing surface 116 includes a termination 155 extending from a proximal end thereof configured to electrically connect to a wire 61 (FIG. 2) extending from a distal end of housing 70. Cutting element 85 includes a termination 165 extending from a proximal end thereof and configured to electrically connect to a wire 62 extending from a distal end of housing 70 (FIG. 2).

As shown in FIGS. 2 and 5, a proximal end of substrate 111 forms a pair of opposing tissue stops 113a, 113b extending therefrom that serve to maintain tissue between sealing surfaces 116, 126 during tissue sealing and prevent tissue from entering the pivot area (e.g., where shaft members 12, 14 rotate about pivot 25). As shown in FIG. 2, tissue stops 113a, 113b are suitably spaced from each other to accommodate the movement of jaw member 44 therebetween relative to jaw member 42. At least one longitudinal indicator 114 (FIG. 5) is formed along the longitudinal length of substrate 111 and includes a distal end 114a that aligns laterally with a distal end of cutting element 85 so that when the jaw members 42, 44 are in the closed configuration (FIG. 6) and the cutting element 85 may not be visible, the user may reference distal end 114a of indicator 114 to determine the position of cutting element 85 relative to tissue grasped between the jaw members 42, 44 prior to energizing cutting element 85 to effect a tissue cut.

Figure 4:
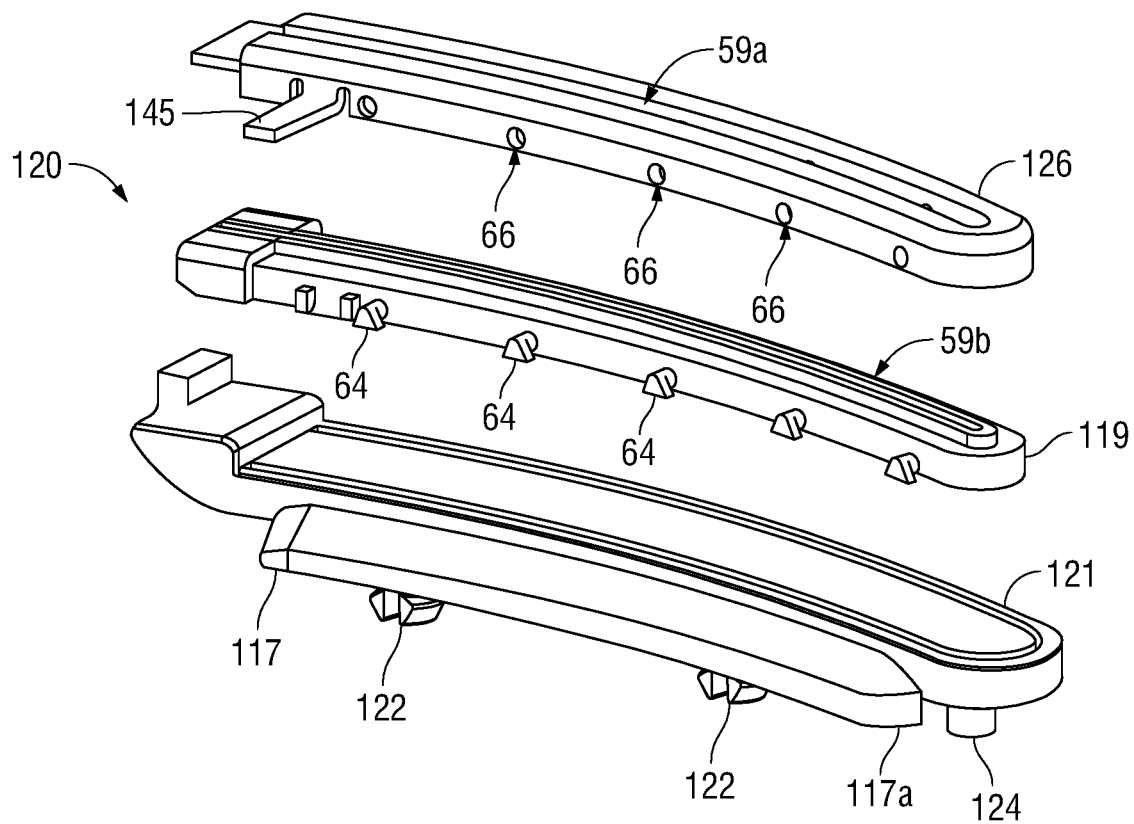
FIGS. 4 and 5 are greatly-enlarged, perspective views of electrodes of the electrode assembly of FIG. 1 with parts separated.

Substantially as described above with respect to electrode 110, and with reference to FIG. 4, electrode 120 includes an electrically conductive sealing surface 126 configured to conduct electrosurgical energy through tissue and a pair of electrically insulative substrates 119 and 121. In some embodiments, substrates 119, 121 are made from an injection molded plastic material. Substrate 121 serves to electrically insulate jaw member 42 from sealing surface 126. A channel 59a is defined in sealing surface 126 and is configured to align in vertical registration with a corresponding gap stop channel 59b defined in substrate 119. Gap stop channel 59b may be formed along substrate 119 such that upon movement of the jaw members 42, 44 to the closed configuration (FIG. 6), cutting element 85 extends through channel 59a in sealing surface 126 and engages gap stop channel 59b to prohibit further approximation of sealing surfaces 116, 126, as further detailed below. Substrate 119 includes retention features 64 formed thereon configured to be received within corresponding retaining apertures 66 disposed along an outer periphery of sealing surface 126 (FIG. 4) to couple sealing surface 126 to substrate 119. During assembly of electrode 120, sealing surface 126 is coupled to substrate 119 and substrate 121 is subsequently overmolded to the retention features 64 formed on substrate 119 to secure sealing surface 126 to substrate 121.

Substrate 121 includes a plurality of bifurcated anchor members 122 extending therefrom that are configured to compress during insertion into a corresponding plurality of sockets 41 disposed at least partially through an inner facing surface 45 (FIG. 3) of jaw member 42 and subsequently expand to releasably engage corresponding sockets 41 after insertion to couple electrode 120 to inner facing surface 45. Substrate 121 also includes an alignment pin 124 (FIG. 4) that is configured to engage an aperture 67 disposed at least partially through inner facing surface 45 of jaw member 42 (FIG. 3) to ensure proper alignment of electrode 120 with jaw member 42 during assembly. Sealing surface 126 includes a termination 145 configured to electrically connect to a wire 63 disposed therein (FIG. 3). In some embodiments, electrodes 110, 120 may be coupled to jaw members 42, 44 before, during, or after assembly of mechanical forceps 20 described above with reference to FIG. 3.

Substrate 121 may also include at least one longitudinal indicator 117 (FIG. 4) formed along the longitudinal length thereof to complement longitudinal indicator 114 of substrate 111. Longitudinal indicator 117 includes a distal end 117a that aligns laterally with a distal end of cutting element 85 so that when the jaw members 42, 44 are in the closed configuration (FIG. 6) and the cutting element 85 may not be visible, the user may reference distal end 117a of indicator 117 to determine the position of cutting element 85 relative to tissue grasped between the jaw members 42, 44 prior to energizing cutting element 85 to effect a tissue cut.

To electrically control the end effector 24, the housing 70 supports at least one depressible activation button 50 (FIG. 1) that is operable by the user to actuate a corresponding electrical switch (not shown) disposed within housing 70 and electrically interconnected with wires 61, 62, and 63. Button 50 may itself be an electrical switch that serves to initiate and terminate delivery of electrosurgical energy from the generator 40 to sealing surfaces 116, 126 to effect a tissue seal and to cutting element 85 to cut sealed tissue. Wires 61, 62, and 63 are bundled to form cable 28, which extends through housing 70 and terminates at a suitable connector (not shown) configured to mechanically and electrically couple to the generator 40.

FIG. 6 shows bipolar forceps 10 during use wherein the shaft members 12 and 14 are approximated to apply clamping force to tissue 150 and to effect a tissue seal. Once sealed, tissue 150 may be cut along the tissue seal by energizing cutting element 85. Cutting element 85 serves to provide a gap distance "G" (FIG. 6) between sealing surfaces 116, 126 during tissue sealing and to cut the tissue along the seal. In some embodiments, cutting element 85 is made from an insulative or non-conductive material and includes a conductive coating disposed thereon. When sealing surfaces 116, 126 are energized during tissue sealing, cutting element 85 may not necessarily be energized so that current is concentrated between sealing surfaces 116, 126 to effectively seal the tissue.

Tissue seal effectiveness may be influenced by the pressure applied to tissue between jaw members 44, 42 and the gap distance between sealing surfaces 116, 126 (FIG. 6) during tissue sealing. Jaw members 42, 44 may be pivoted about pivot 25 to move jaw members 42, 44 to the closed configuration of FIG. 6 wherein sealing surfaces 116, 126 provide a pressure to tissue grasped therebetween. In some embodiments, to provide an effective seal, a pressure within a range between about 3 kg/cm$^2$ to about 16 kg/cm$^2$ is applied to tissue and, in other embodiments, a pressure within a range between about 7 kg/cm$^2$ to about 13 kg/cm$^2$ is applied to the tissue. In the closed configuration of jaw members 42, 44, gap distance "G" may be maintained between sealing surfaces 116, 126 by cutting element 85. Cutting element 85 extends through channel 59a of sealing surface 126 and engages stop gap channel 59b (FIG. 4) defined in substrate 119 to prohibit further approximation of sealing surfaces 116, 126 and to create gap distance "G" (FIG. 6) between sealing surface 116, 126 during tissue sealing. In some embodiments, to provide an effective tissue seal, an appropriate gap distance of about 0.001 inches to about 0.010 inches and, in other embodiments, between about 0.002 and about 0.005 inches may be provided.

Cutting element 85 may be independently activated by the surgeon or automatically activated by generator 40 once tissue sealing is complete. Generator 40 may employ a suitable safety algorithm to assure that an accurate and complete tissue seal is formed before cutting element 85 is energized to cut tissue. An audible or visual indicator (not shown) may be employed to assure the surgeon that an effective tissue seal has been achieved and the surgeon may be required to press button 50 again or deactivate a safety mechanism (not shown) to initiate tissue cutting.

In some embodiments, tissue sealing and tissue cutting may be completed using a single activation step without the need to re-grasp tissue between sealing surfaces 116, 126 or without the need to perform a second activation step (e.g., pressing button 50 disposed on housing 70) to initiate tissue cutting following completion of tissue sealing. For example, generator 40 may be configured with a suitable tissue sealing and/or tissue cutting control algorithm that allows tissue sealing and tissue cutting to be performed in response to a single activation step, i.e., the pressing of button 50 disposed on housing 70. In this scenario, the tissue sealing process is started and completed following activation of button 50. A first audible tone may be emitted by generator 40 to signal the completion of the tissue sealing process. Generator 40 next initiates the tissue cutting process to cut the previously sealed tissue and, upon completion of the tissue cutting process, emits a second audible tone (e.g., a tone different than the first tone) to signal the completion of the tissue cutting process. In some embodiments, generator 40 includes a suitable user interface configured to allow a user to switch generator 40 between a tissue cut only mode, a tissue seal only mode, or a combined tissue cut and tissue seal mode that allows tissue sealing and cutting in response to a single activation step, as described above.

According to one aspect of the present disclosure, a method of manufacturing a forceps (e.g., mechanical forceps 20) includes press-fitting a first surface of a pivot (e.g., pivot 25) into an aperture defined in a first shaft member (e.g., shaft member 12) and pressing a second surface of the pivot into an aperture defined through a first jaw member (e.g., jaw member 44) disposed on a second shaft member (e.g., shaft member 14). The method also includes pressing a third surface of the pivot into an aperture defined through a second jaw member (e.g., jaw member 42) such that the pivot is disposed to provide separation between the jaw members. The method also includes coupling a distal end portion of the first shaft member to the second jaw member. The method may also include coupling an electrode (e.g., electrode 110 or 120) to at least one of the jaw members. The electrode may include at least one of a tissue sealing surface (e.g., tissue sealing surface 116 or 126), an insulative substrate (e.g., substrate 109, 111, 119, or 121) and an electrically conductive cutting element (e.g., cutting element 85). The method may also include welding the distal end portion of the first shaft member to the second jaw member. The method may also include coupling a housing (e.g., housing 70) to at least one of the shaft members.

Figure 7:
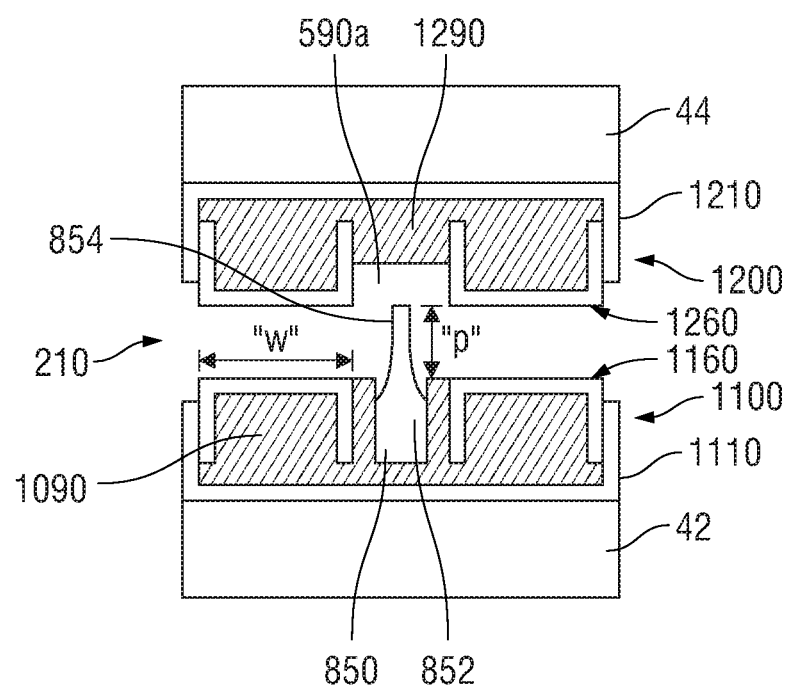
FIG. 7 is a transverse, cross-sectional view of another electrode assembly configured for use with the bipolar forceps of FIG. 1.

Turning now to FIG. 7, another electrode assembly 210 provided in accordance with the present disclosure and configured for use with bipolar forceps 10 (FIG. 1) is shown. Electrode assembly 210 may include any or all of the features of electrode assembly 21 (FIGS. 2, 4, and 5), described above. Likewise, electrode assembly 21 (FIGS. 2, 4, and 5) may incorporate any or all of the features of electrode assembly 210. Electrode assembly 210 is described in detail below.

Electrode assembly 210 generally includes first and second electrodes 1100, 1200, respectively. First electrode 1100 includes an electrically conductive sealing surface 1160 configured to conduct electrosurgical energy through tissue to effect a tissue seal, an electrically conductive cutting element 850 configured to cut tissue by conducting electrosurgical energy therethrough, and a pair of electrically insulative substrates 1090 and 1110. Substrate 1090 is disposed between sealing surface 1160 and cutting element 850 and serves to electrically insulate sealing surface 1160 from cutting element 850. Substrate 1110 serves to electrically insulate jaw member 42 from sealing surface 1160 and cutting element 850. Cutting element 850 is disposed within and extends from substrate 1090 such that cutting element 850 extends beyond or is raised above a tissue contacting portion of sealing surface 1160. More specifically, cutting element 850 may be configured to extend from the tissue contacting portion of sealing surface 1160 between about 0.004" and about 0.010". That is, cutting element 850 may define a prominence "P" of between about 0.004" and about 0.010". Further, the ratio of the prominence "P" of cutting element 850 to the width "W" of each portion of sealing surface 1160 may be between about 0.25 to about 0.30. For example, for a width "W" of about 0.25", the prominence "P" may be about 0.007". Other prominence configurations are also contemplated. It has been found that a prominence "P" of between about 0.004" and about 0.010" provides increased cut performance, particularly with respect to thicker and/or more fatty tissue.

Cutting element 850 includes a base portion 852 substantially disposed within substrate 1090, and a body portion 854 extending from substrate 1090 towards the opposed jaw member 42. Base portion 852 defines a greater width than body portion 854 to inhibit cutting element 850 from sinking into substrate 1090, e.g., to inhibit variation in the prominence of cutting element 850. The width of base portion 852 may be at least about 0.022", while the minimum width of body portion 854 may be about 0.015", although other configurations are also contemplated.

Electrode 1200 includes an electrically conductive sealing surface 1260 configured to conduct electrosurgical energy through tissue and a pair of electrically insulative substrates 1290 and 1210. Substrate 1210 serves to electrically insulate jaw member 44 from sealing surface 1260. Substrate 1290 extends into a channel 590a defined in sealing surface 1260 and is configured to align in vertical registration with cutting element 850 to electrically insulate cutting element 850 from sealing surface 1260. Substrate 1290 may be recessed relative to a tissue contacting portion of sealing surface 1260 or may be substantially flush therewith. More specifically, substrate 1290 may be recessed within channel 590a and relative to the tissue contacting portion of sealing surface 1260 by up to about 0.006", although no recess is also contemplated. Further, the recessed distance of substrate 1290 (or lack or recession of substrate 1290) and the prominence of cutting element 850 may cooperate to establish a minimum gap distance between electrodes 1100, 1200 when approximated relative to one another. The minimum gap distance may be about 0.004", although other gap distances are also contemplated. Thus, for example, the prominence of cutting element 850 may be about 0.007" and the recessed distance of substrate 1190 may be about 0.003" to establish a minimum gap distance of about 0.004", although other configurations are also contemplated. As can be appreciated, this combination of a recessed substrate 1190 and prominent cutting member 850 provides the benefit or a prominent cutting member 850, as detailed above, while maintaining a desired minimum gap distance.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A bipolar forceps, comprising:
    a mechanical forceps including first and second shafts each having a jaw member extending from a distal end thereof and a handle disposed at a proximal end thereof for effecting movement of the jaw members relative to one another about a pivot from a first position wherein the jaw members are disposed in spaced relation relative to one another to a second position wherein the jaw members cooperate to grasp tissue therebetween;
    a disposable housing configured to releasably couple to at least one of the shafts;
    an electrode assembly having a first electrode releasably coupleable to the jaw member of the first shaft and a second electrode releasably coupleable to the jaw member of the second shaft, each electrode having an electrically conductive sealing surface adapted to connect to a source of electrosurgical energy to allow selective conduction of electrosurgical energy through tissue held therebetween to effect a tissue seal;
    an electrically conductive cutting element disposed on the first electrode and adapted to connect to the source of electrosurgical energy to allow selective conduction of electrosurgical energy through tissue held between the electrodes to effect a tissue cut; and
    a first insulative substrate configured to releasably couple the first electrode to the jaw member of the first shaft and a second insulative substrate different than the first insulative substrate disposed between the first insulative substrate and the electrically conductive sealing surface of the first electrode, the first insulative substrate extending along a side surface of the second insulative substrate, the conductive cutting element disposed between the first and second insulative substrates and extending through a longitudinal channel defined by the second insulative substrate and a longitudinal channel defined by the electrically conductive sealing surface of the first electrode when the jaw members are disposed in the first position.

2. The bipolar forceps according to claim 1, wherein the second electrode includes an insulative substrate defining a longitudinal channel disposed in vertical registration with the conductive cutting element and configured to engage the conductive cutting element when the jaw members are in the second position to provide a gap distance between the electrodes.

3. The bipolar forceps according to claim 2, wherein the conductive cutting element extends from the first electrode a distance between about 0.004" and about 0.010" and wherein the longitudinal channel defined by the insulative substrate of the second electrode defines a depth of up to about 0.006".

4. The bipolar forceps according to claim 3, wherein the extension distance of the conductive cutting element and the depth of the longitudinal channel defined by the insulative substrate of the second electrode cooperate to provide a gap distance of about 0.004".

5. The bipolar forceps according to claim 1, further comprising at least one switch disposed through the housing configured to selectively deliver electrosurgical energy to at least one of the electrically conductive cutting element or the electrically conductive sealing surfaces.

6. The bipolar forceps according to claim 5, wherein the switch is configured to selectively deliver electrosurgical energy to the electrically conductive sealing surfaces and the electrically conductive cutting element in response to a single activation thereof.

7. The bipolar forceps according to claim 1, wherein a ratio of a prominence of the conductive cutting element to half a width of the electrically conductive sealing surface of the first electrode is between about 0.25 and about 0.30.

8. The bipolar forceps according to claim 1, wherein the conductive cutting element defines a base portion and a body portion, the base portion defining a width of at least 0.022" and the body defining a minimum width of about 0.015".

9. The bipolar forceps according to claim 1, wherein the pivot includes a first surface configured to be received in an aperture defined through the first jaw member and a second surface configured to be received in an aperture defined through the second jaw member.

10. The bipolar forceps according to claim 1, wherein each of the electrodes includes at least one mechanical interface configured to complement a corresponding mechanical interface on one of the jaw members to releasably couple the electrode to the respective jaw member.

11. The bipolar forceps according to claim 1, further comprising a tissue stop disposed at a proximal end of at least one of the jaw members and configured to maintain tissue between the electrodes during tissue sealing.

12. The bipolar forceps according to claim 1, wherein at least a portion of the second insulative substrate is disposed within the longitudinal channel defined by the electrically conductive sealing surface of the first electrode.

13. The bipolar forceps according to claim 1, further comprising a tissue stop disposed at a proximal portion of at least one of the jaw members and configured to prevent tissue from entering the pivot.

14. A bipolar forceps, comprising:
    a mechanical forceps including first and second shafts each having a jaw member extending from a distal end thereof and a handle disposed at a proximal end thereof for effecting movement of the jaw members relative to one another about a pivot from a first position wherein the jaw members are disposed in spaced relation relative to one another to a second position wherein the jaw members cooperate to grasp tissue therebetween;
    a disposable housing having opposing halves configured to be releasably coupled to each other to at least partially encompass at least one of the shafts;
    an electrode assembly having a first electrode releasably coupleable to the jaw member of the first shaft and a second electrode releasably coupleable to the jaw member of the second shaft, each electrode having an electrically conductive sealing surface defining a longitudinal channel and adapted to connect to a source of electrosurgical energy to allow selective conduction of electrosurgical energy through tissue held therebetween to effect a tissue seal;
    an electrically conductive cutting element disposed on the first electrode and adapted to connect to the source of electrosurgical energy to allow selective conduction of electrosurgical energy through tissue held between the electrodes to effect a tissue cut;
    each of the first and second electrodes including a first insulative substrate configured to releasably couple the electrode to one of the jaw members and a second insulative substrate different than the first insulative substrate disposed between the first insulative substrate and the electrically conductive sealing surface, the first insulative substrate disposed on a side surface of the second insulative substrate, the electrically conductive cutting element disposed between the first and second insulative substrates of the first electrode and extending through a longitudinal channel defined by the second insulative substrate of the first electrode and the longitudinal channel defined by the electrically conductive sealing surface of the first electrode when the jaw members are disposed in the first position, wherein the electrically conductive cutting element extends through the longitudinal channel defined by the electrically conductive sealing surface of the second electrode and into engagement with a longitudinal channel defined by the second insulative substrate of the second electrode to control a gap between the jaw members when the jaw members are in the second position; and at least one switch disposed on the housing configured to selectively deliver electrosurgical energy to at least one of the electrically conductive cutting element and the electrodes.

15. The bipolar forceps according to claim 14, wherein the switch is configured to selectively deliver electrosurgical energy to the electrically conductive sealing surfaces and the electrically conductive cutting element in response to a single activation thereof.

16. The bipolar forceps according to claim 15, wherein the source of electrosurgical energy is configured to emit a first audible tone in response to completion of the tissue seal and a second audible tone in response to completion of cutting of the sealed tissue.

17. The bipolar forceps according to claim 14, wherein at least a portion of the jaw members are separated by the pivot.

18. A bipolar forceps, comprising:

a first jaw member coupled to a first shaft and a second jaw coupled to a second shaft, the first and second shafts movable about a pivot to move the first and second jaw members relative to each other between an open position and a closed position;

a first electrode releasably coupled to the first jaw member and a second electrode releasably coupled to the second jaw member, the first electrode including:

a tissue sealing surface defining a longitudinal channel and adapted to connect to a source of electrosurgical energy;

a first insulator configured to releasably couple the tissue sealing surface to the first jaw member; and a second insulator different than the first insulator defining a longitudinal channel and disposed at least partially within the longitudinal channel defined by the tissue sealing surface, the first insulator extending along a side surface of the second insulator; and a cutting element disposed on the first jaw member and configured to electrosurgically cut tissue, the cutting element extending through the longitudinal channel defined by the second insulator and the longitudinal channel defined by the tissue sealing surface of the first electrode.

19. The bipolar forceps according to claim 18, wherein the cutting element extends through the longitudinal channel defined by the second insulator and the longitudinal channel defined by the tissue sealing surface of the first electrode when the jaw members are in the open position.

20. The bipolar forceps according to claim 1, wherein the second insulative substrate is disposed adjacent to the electrically conductive cutting element and between the electrically conductive cutting element and the electrically conductive sealing surface of the first electrode to insulate the electrically conductive cutting element from the electrically conductive sealing surface of the first electrode.

* * * * *